(12) United States Patent
Petty

(10) Patent No.: US 6,691,562 B2
(45) Date of Patent: Feb. 17, 2004

(54) TEST FOR BRAKE FLUID AGE AND CONDITION

(75) Inventor: Jon A. Petty, Tucson, AZ (US)

(73) Assignee: Phoenix Systems, L.L.C., Tucson, AZ (US)

( * ) Notice: Subject to any disclaimer, the term of this patent is extended or adjusted under 35 U.S.C. 154(b) by 0 days.

(21) Appl. No.: 10/132,978

(22) Filed: Apr. 26, 2002

(65) Prior Publication Data

US 2002/0129644 A1 Sep. 19, 2002

Related U.S. Application Data (63) Continuation-in-part of application No. 10/030,455, filed as application No. PCT/US00/19892 on Jul. 20, 2000.
(60) Provisional application No. 60/144,686, filed on Jul. 20, 1999.

(51) Int. Cl.$^7$ ............................................. G01N 25/00
(52) U.S. Cl. ................................................ 73/61.46
(58) Field of Search ............................ 73/61.46, 61.77, 73/61.76, 61.41, 61.42, 53.01, 39; 422/82.12, 61, 86, 87; 374/16, 27, 57, 45; 701/29

(56) References Cited

U.S. PATENT DOCUMENTS

| | | | |
|---|---|---|---|
| 3,081,619 A | 3/1963 | Pappas | 73/17 |
| 3,698,236 A | 10/1972 | Markey | 73/17 A |
| 3,844,159 A | 10/1974 | Mitzutani | 73/17 A |
| 4,059,006 A | 11/1977 | Mizutani et al. | 73/17 A |
| 4,059,407 A * | 11/1977 | Hochstrasser | 23/253 TP |
| 4,198,207 A * | 4/1980 | Ladov et al. | 23/230 HC |
| 4,484,823 A | 11/1984 | Peuker | 374/27 |
| 4,589,277 A * | 5/1986 | Collins et al. | 73/61.46 |
| 4,970,172 A * | 11/1990 | Kundu | 436/130 |
| 5,182,942 A * | 2/1993 | Hartel et al. | 73/61.46 |
| 5,380,091 A | 1/1995 | Buchanan | 374/16 |
| 5,433,105 A * | 7/1995 | Takahashi et al. | 73/61.46 |
| 5,518,933 A | 5/1996 | Ishibashi | 436/163 |
| 5,620,658 A * | 4/1997 | Jaunakais | 422/58 |
| 5,814,721 A | 9/1998 | Mills | 75/53.01 |
| 5,969,808 A * | 10/1999 | Cotton et al. | 356/135 |
| 6,119,059 A * | 9/2000 | Tai et al. | 701/29 |
| 6,145,468 A * | 11/2000 | Woog | 116/206 |

* cited by examiner

Primary Examiner—Hezron Williams
Assistant Examiner—J L Politzer
(74) Attorney, Agent, or Firm—Antonio R. Durando (57) ABSTRACT

A correlation is derived between a variable, defined as "virtual age," indicative of brake fluid's service age and/or mileage and the concentration of copper in the fluid. Virtual age is utilized to estimate the degree of degradation of the fluid. A reactive test strip is used to measure the concentration of copper ions in the brake fluid in terms of a readily visible color change. The strip is immersed in the fluid and any resulting color change is compared to a color chart and a standard representative of the maximum concentration determined empirically to correspond to the desirable "virtual-age" threshold for fluid replacement. An automated embodiment of the invention includes an optical instrument to compare the color obtained from the test to a predetermined standard and determine whether a fluid change is recommended.

20 Claims, 8 Drawing Sheets

Actual Test results using atomic plasma spectroscopy compared with test strip readings

| 0-ppm Cu | 9-ppm Cu | 30-ppm Cu | 154-ppm Cu | 365-ppm Cu |
|---|---|---|---|---|
|  |  |  |  |  |

10

20

0  10  30  100  300
ppm Copper
Test Key

TEST FOR BRAKE FLUID AGE AND CONDITION

RELATED APPLICATIONS

This application is a continuation-in-part of U.S. Ser. No. 10/030,455, filed Jan. 3, 2002, as a national-stage application of International Application PCT/US00/19892, filed Jul. 20, 2000, which was based on U.S. Provisional Application No. 60/144,686, filed Jul. 20, 1999.

BACKGROUND OF THE INVENTION

1. Field of the Invention

This invention is related in general to methods and devices for testing the condition of automotive brake fluid. In particular, the invention pertains to a novel and different approach based on a correlation between brake-fluid condition and the concentration of specific metals in the fluid, in particular copper, iron, and zinc.

2. Description of the Related Art

Brake fluid is used to transmit the pressure exerted on a motor vehicle's brake pedal to the slave cylinders of the braking system. The most commonly used brake fluids consist of glycol-based liquids categorized as DOT3 and DOT4 on the basis of the boiling point resulting from their particular composition. In order to prevent boiling of the fluid caused by overheating during use, DOT3 and DOT4 fluids are required to have a dry boiling point (with no moisture in fluid) of at least 401° F. (205° C.) and 446° F. (230° C.), respectively, so that proper brake operation is ensured under all temperature conditions. A low boiling point can cause the brake fluid to vaporize under hot operating conditions, such as during continuous braking on a downhill road. Such vaporization can create pockets of compressible vapor in the system that dangerously reduce the effectiveness of the braking system. This is the occurrence normally referred to as "brake fade" which, in extreme cases, can cause complete brake failure.

All types of glycol-based brake fluid are hygroscopic. As a result of this property, they readily absorb moisture that reduces their boiling point and, if unchecked, can become dangerous. Thus, replacement of DOT3 and DOT4 fluids is desirable when they have absorbed enough moisture to decrease their vaporization temperatures to about 284° F. (140° C.) and 311° F. (155° C.), respectively, which are minimum acceptable wet boiling points (with moisture absorbed by the fluid) empirically considered safe for brake operation and established as such by the U.S. Department of Transportation. Since the moisture content of brake fluid increases with age and exposure to ambient humidity, it is clear that it should be checked periodically and that the fluid should be replaced when its boiling point approaches these safety limits.

Copending U.S. Ser. No. 10/030,455, hereby incorporated by reference, discloses a novel approach for estimating the boiling point of brake fluid based on the discovery that moisture content is closely correlated to the copper content in the fluid. The invention consists of a reactive test strip adapted to measure and indicate the concentration of copper ions in brake fluid in terms of a readily visible color change. The strip is immersed in the fluid and the resulting color acquired by reacting with the fluid is compared to a copper concentration-versus-color chart or to a standard color representative of the maximum concentration determined empirically to correspond to a boiling point considered safe for normal operation. If the color change indicates a higher-than-desirable copper concentration, the brake fluid is considered inadequate for safe operation and replaced without further tests. A similar strip is disclosed for measuring iron concentration, which, as well as zinc, is another metal found to provide a useful correlation with the moisture content of the brake fluid.

Another important aspect of brake systems maintenance is the corrosive nature of some of their constituents, which, upon contamination of the brake fluid, progressively contribute to damage metallic tubing and other parts of the brake system. In conventional fluids, amines are added to inhibit corrosion and prevent damage to metal parts that operate in contact with the fluid. As the brake fluid ages, its anticorrosive properties are measured in terms of reserve alkalinity; that is, the amount of amines remaining in the fluid to buffer the acidity resulting from breakdown of fluid constituents. Over time, thermal oxidation and volatization produce a significant reduction of the amine content and the concurrent decrease of anticorrosive properties. Tests have shown that the reserve alkalinity of DOT3 and DOT4 fluids is reduced to about 20 percent of its original value after 18 to 20 months of normal operation. Therefore, brake fluids also need to be checked and periodically replaced in order to prevent dangerous corrosion in the brake system. Accordingly, industry maintenance recommendations are typically based on service time and milage of the vehicle.

This invention constitutes a further advance in the art based on the recognition that the copper content in brake fluid is predictably related not only to moisture content but also to time and mileage of vehicle operation. Thus, this correlation can be advantageously used to estimate milestones for maintenance purposes without regard to actual service time and/or mileage. Instead, copper content is adopted as a reliable indicator of a vehicle's "virtual age," a term used to refer to the wear and tear on brake fluid resulting from actual mileage and/or time of service.

BRIEF SUMMARY OF THE INVENTION

The primary objective of this invention is a method and a test kit for determining whether the brake fluid in a vehicle has reached a state of deterioration corresponding to a predetermined time and/or mileage considered to be a threshold warranting replacement as a matter of scheduled maintenance.

Another objective of the invention is a method and apparatus for assessing the condition of the fluid's degree of contamination, and correspondingly its remaining anticorrosive properties, with a test similar to the one performed to determine its boiling point.

Another goal is a test that does not require retrieval of a sample of fluid from the braking system and does not involve elaborate testing procedures.

Yet another goal is a procedure that can be carried out rapidly during regular automotive maintenance.

A final objective is a procedure that can be implemented easily and economically according to the above stated criteria.

Therefore, according to these and other objectives, a normalized correlation between the concentration of copper in brake fluid and its service age and/or mileage has been developed and utilized to estimate the degree of degradation of the fluid. In its preferred embodiment, the invention consists of a reactive test strip adapted to measure and indicate the concentration of copper ions in brake fluid in terms of a readily visible color change. The strip is immersed in the fluid and the resulting color acquired by reaction with the fluid is compared to a copper concentration-versus-color chart or to a color standard representative of the concentration determined empirically to correspond to the desirable "virtual-age" threshold for fluid replacement or other maintenance. If the color change indicates a higher-than-acceptable copper concentration, the brake fluid is considered degraded and contaminated, and therefore also corrosive and in need of replacement for proper maintenance of the vehicle's braking system. An automated embodiment of the invention includes an optical instrument to compare the color obtained from the test to a predetermined standard and determine whether a fluid change is recommended. According to other, less preferred, embodiments of the invention, similar correlations are derived between concentrations of iron and zinc and the virtual age of brake fluid.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only some of the various ways in which the invention may be practiced.

DESCRIPTION OF THE PREFERRED EMBODIMENTS OF THE INVENTION

This invention is based on the realization that the brake-fluid concentration of copper, the principal metal previously disclosed as being predictably correlated to the degradation of the fluid's boiling point and reserve alkalinity, is also indicative of the fluid's service age and/or mileage; that is, the vehicle's virtual age. Accordingly, this correlation between service age and/or mileage and copper concentration is advantageously used to estimate the condition of the fluid and establish maintenance schedules based thereon.

Most brake lines consist of steel lined with a copper alloy and represent the largest surface area of metal in contact with brake fluid. A typical light-duty vehicle uses about 14 meters of such tubing with an inside diameter of about 2.5 mm, for a total internal surface area of about 1,200 $cm^2$. Therefore, corrosion of these lines contributes relatively large amounts of copper ions to the fluid. The master and slave cylinders include steel components that are also susceptible to corrosion as the fluid ages, its water content increases and its reserve alkalinity decreases. Dissolved iron is also known to appear in brake fluid after the initial amine corrosion inhibitor is significantly depleted and the dissolved copper level reaches about 200 ppm. By the time this event occurs, the fluid is highly corrosive and damaging to the system, and its replacement is long overdue regardless of its actual service time or mileage.

New DOT3 and DOT4 fluids contain about 0.5 ppm copper, 6 ppm iron, and 0.6 ppm zinc. Since the concentration of these metals is known to increase substantially after an initial period of brake fluid operation, this invention is based on the idea of correlating these metal concentrations in the fluid with the fluid's "virtual age," the coined term used as a measure of a normalized combination of mileage and time of service, such that these metal concentrations can be used as indicators of the fluid's service age and/or time of use.

Accordingly, for the purpose of this invention, "virtual age" of a brake fluid is defined as a measure of fluid condition corresponding to either actual service age or actual service mileage, or a combination of the two. Since it is known that the condition of brake fluid deteriorates with use as well as with time alone, the notion of virtual age is used as a normalized age variable to measure either or both as a function of metal content in the fluid (preferably copper).

Figure 1:
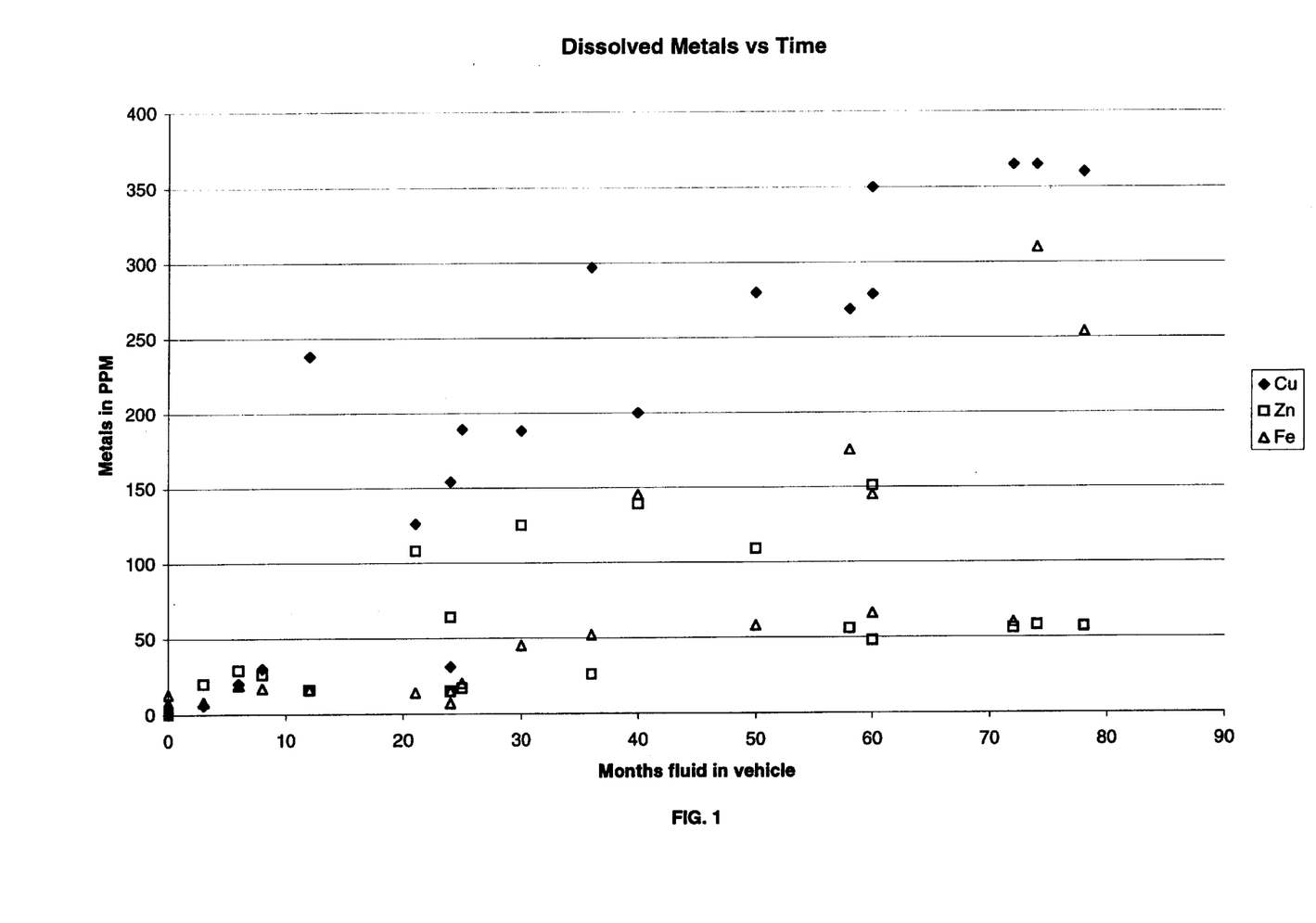
FIG. 1 is a plot showing the relationship between copper, iron and zinc content and service age of brake fluid based on a variety of vehicles and commercial brake fluids.
Figure 2:
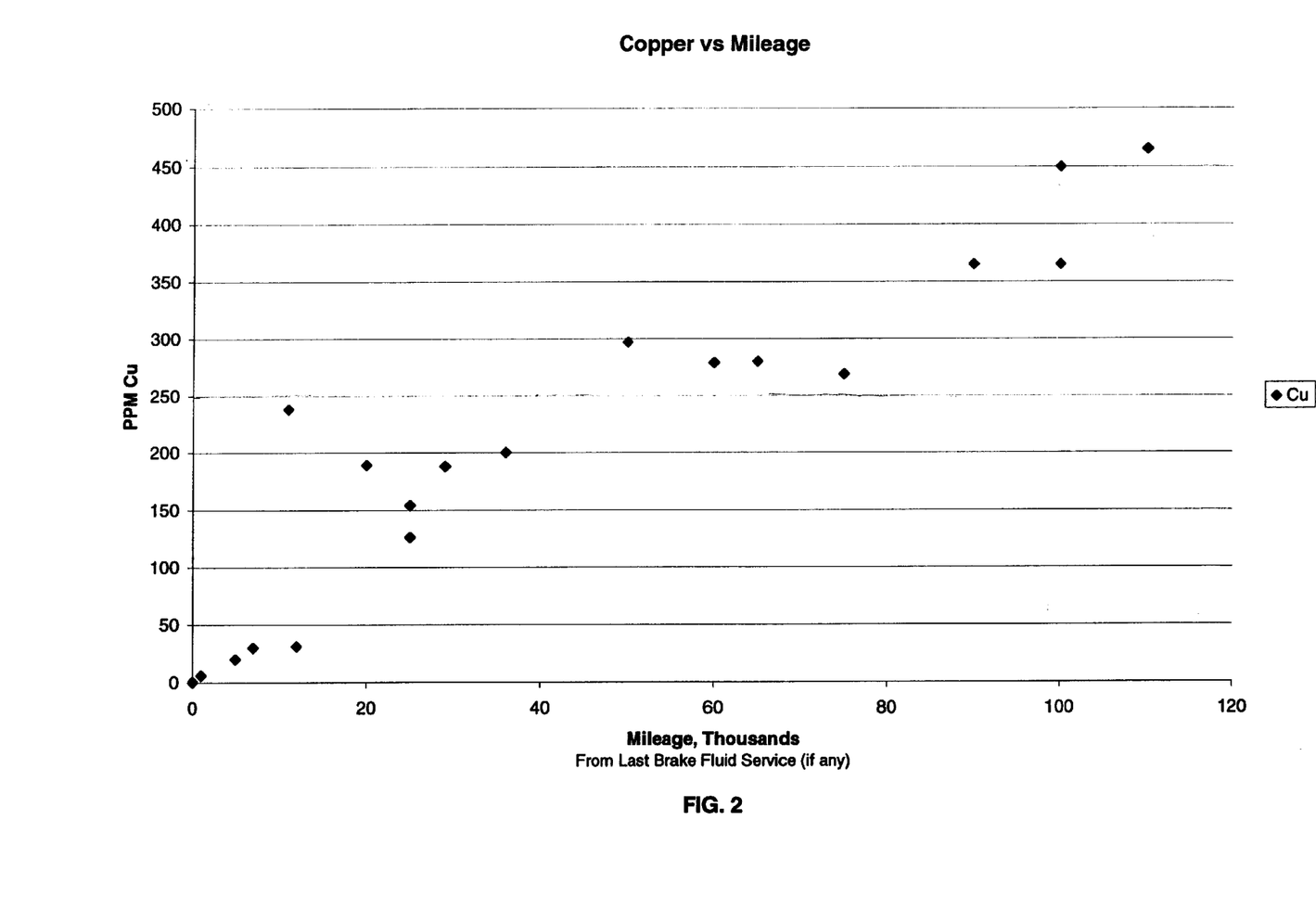
FIG. 2 is a plot showing the relationship between copper content and service mileage of brake fluid based on a variety of vehicles and commercial brake fluids.

FIGS. 1 and 2 illustrate the high degree of correlation between copper content and actual fluid age and copper content and mileage, respectively. (FIG. 1 also shows a less pronounced correlation with iron and zinc.) Many vehicle manufacturers recommend replacement of brake fluid after 24,000 miles or two years of operation. Thus, various brake fluids in many different vehicles subjected to normal operating conditions (defined as about 1,000 miles per month, mostly city driving with occasional long trips) were tested for copper content after 24,000 miles of operation; and the same was done with vehicles having two years of brake-fluid operation under the same conditions. It was found that the copper content in both cases had risen to about the same level, approximately 150 ppm. Therefore, this level of copper in the brake fluid was used according to the invention as an indicator of a two-year virtual age corresponding to either 24,000 miles or two years of actual operation. Thus, the virtual age was adopted to provide an indication of when the fluid should be replaced according to manufacturer recommendation (that is, when the fluid had reached a condition corresponding to the 24,000 miles or two-year usage threshold).

Similar tests were conducted with various other vehicles known to have been subjected to abnormal driving conditions, such as high-performance cars that were driven particularly harshly and less performing cars driven mostly on long trips. The fluid was analyzed for water, amine (alkalinity), copper and iron content, which are well recognized in the prior art as reliable indicators of fluid deterioration, at the 24,000-mile and 24-month target. Seven other metals were also tested, but no significant correlation was identified. As expected, it was found that the condition of the brake fluid in the first group of vehicles had deteriorated to the point of warranting a change way before, and the fluid in the second group of vehicles way after, the 24,000 miles or two-year thresholds recommended for maintenance by the manufacturers. Thus, the service age and mileage of the brake fluid in these vehicles were normalized to those of the normally operated vehicles by assigning a virtual age of 24 months to the data points corresponding to a copper content of 150 ppm. Similar tests were done with vehicles equipped with antilock brake systems (ABS), where the brake-fluid recirculation circuit fastens fluid degradation, and the fluid condition was found to closely parallel that found in harshly drive vehicles. That is, it was determined that about 150 ppm of copper in the brake fluid correlates advantageously with the fluid condition recommended for replacement at the 24,000 mile/two-year regular maintenance of the brake system.

Figure 3:
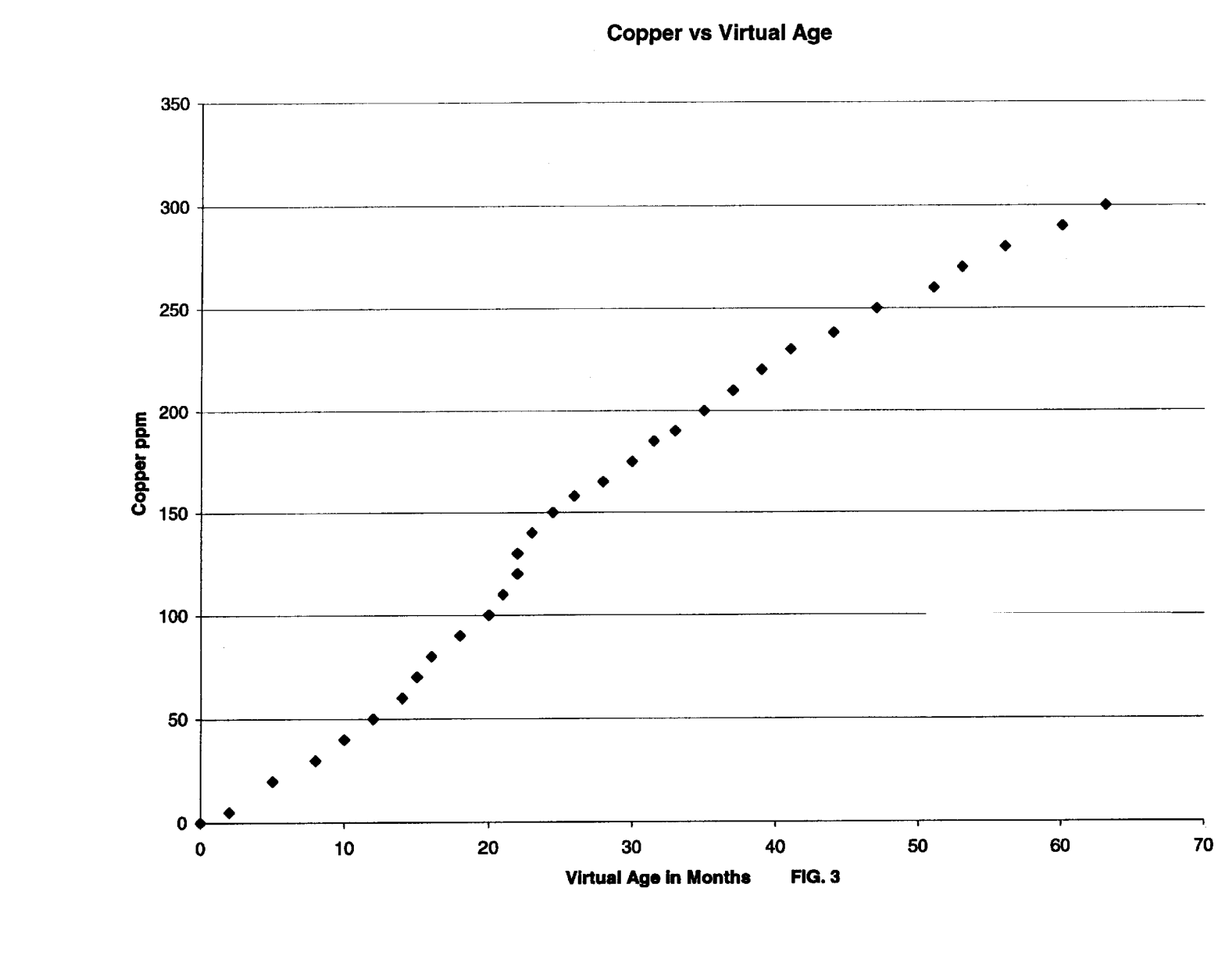
FIG. 3 is an empirically derived plot of brake-fluid copper content versus virtual age, used to estimate maintenance thresholds according to the invention.

Analyses of these used brake fluids consistently illustrated that virtual age is predictably correlated to the degradation of the performance and anti-corrosive properties of the fluid. By repeating the same tests and analyses for different periods of time and mileage of operation, it was possible to track the concentration of copper as it varies for different periods of actual time and mileage of operation, so that different recommended maintenance milestones (such as 36,000 miles or three years, for example) could be expressed in terms of virtual age and a corresponding level of copper concentration. FIG. 3 is a plot of the correlation between virtual age and copper concentration derived from these experiments.

It is noted that the brake fluids tested were sampled from vehicles that had been in operation for a number of years. No differentiation was made between DOT3 and DOT4 fluids because the two are perfectly miscible (both are glycol based) and in practice they can be used interchangeably in motor vehicles, especially by drivers who choose to service their brakes themselves. Therefore, some vehicles'brake systems contain a mixture of the two after some time of operation and maintenance. Since the invention was developed to produce a test for use primarily by auto mechanics during routine maintenance of brake systems, which may include a mixture of the two types of fluids, it made sense to develop correlations that relate metal contents to the fluid's virtual age in terms of unspecified fluid type.

Thus, based on these results and as a further refinement to the invention disclosed in Ser. No. 10/030,455, it became clear that a useful correlation exists between copper concentration and virtual age of brake fluids. This correlation can be advantageously used to test brake fluid because the copper content, in addition to being a contaminant, is also a good indicator of the condition of the fluid with reference to the time and/or mileage thresholds recommended for scheduled maintenance. Accordingly, the device of the invention consists of a test strip for measuring the copper content of the brake fluid. The strip includes a reactive component that changes color as a function of metal concentration in the fluid. The strip is immersed in the brake fluid and allowed to react for the required amount of time to reach equilibrium; then, it is compared to a standard color-versus-concentration chart to determine the current metal concentration in the fluid and its corresponding condition. If the strip color matches or surpasses the color standard corresponding to a virtual age set as a threshold for fluid replacement, as recommended by a manufacturer or determined empirically by a user, the appropriate maintenance course of action is taken. Thus, this test can be used to readily establish maintenance requirements.

Figure 4:
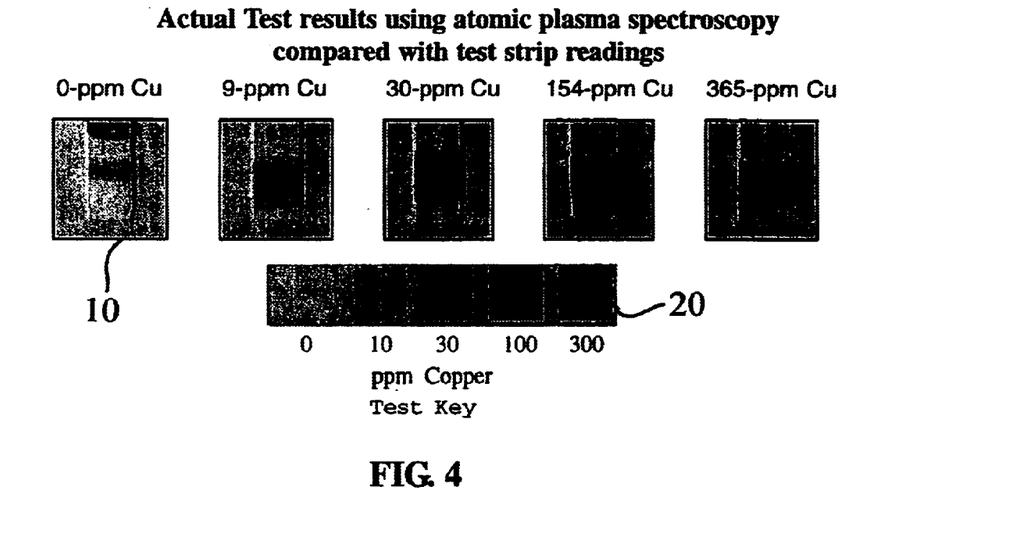
FIG. 4 is a view of the tip of the reactive strip of the invention next to a standard chart of strip color as a function of metal concentration in the brake fluid illustrating the color identification process of the invention.

Strips suitable to practice the invention are manufactured by EM Science, a division of EM Industries, Inc. For example, as illustrated in FIG. 4, the strip 10 sold as EM Quant™ varies in color from white to dark purple, with shades of increasingly dark purple corresponding to progressively higher copper concentrations ranging from 0 to 300 ppm. The color of the strip 10 is compared to a test chart 20 to determine the approximate copper concentration in the fluid. In practice, a color change corresponding to a copper concentration of about 150 ppm was found to be a safe indicator of the 24,000-mile/two-year condition of the brake fluid for maintenance purposes. Similarly, a color change corresponding to a copper concentration of about 200 ppm was found to be a safe indicator of the 36,000-mile/three-year condition of the brake fluid. Thus, the plot of FIG. 3 and the strips of the invention can be used in equivalent fashion to estimate the copper level corresponding to any other mileage/time maintenance standard set by a manufacturer.

It is noted that the white-to-purple color change of copper test strips is stable and retains its shade long after the test is complete. Accordingly, the test strip can be examined for an assessment long after the test has been completed and it can be retained to show the results at a later time to a customer or other interested party. Moreover, the copper strips are not subject to deterioration from exposure to ambient conditions.

According to another aspect of the invention, an automated device could be used to compare the color change in a test strip with the standard chart of the invention. For example, a reflectometer, such as sold by EM Industries Inc. of Gibbstown, N.J., under the trademark RQflex®, can be readily utilized after calibration for the specific purpose of the invention. It includes test strips for particular metals of interest, a meter for detecting the metal concentration as a function of color change in the strip, a digital read-out, and programmable functions. The device provides quantifiable results simply by dipping a test strip in the brake fluid and then inserting it in the meter. The concentration of the metal of interest, such as copper, is read directly on a digital display. By correlating the metal concentration with the virtual age of the brake fluid according to the invention, which can be done by appropriately programming the meter, a determination of whether a milestone for required maintenance has been reached can be made rapidly and consistently according to the invention. Thus, such a device removes any subjectivity from the test. The device could also be interfaced with a computer to allow data communication for storage and printout purposes. Furthermore, a data base could be added to a computerized device to collect information based on currently tested vehicles and to use this feedback to adjust the standard of comparison as a function of a vehicle's specific brake system, if that is deemed necessary.

Figure 5:
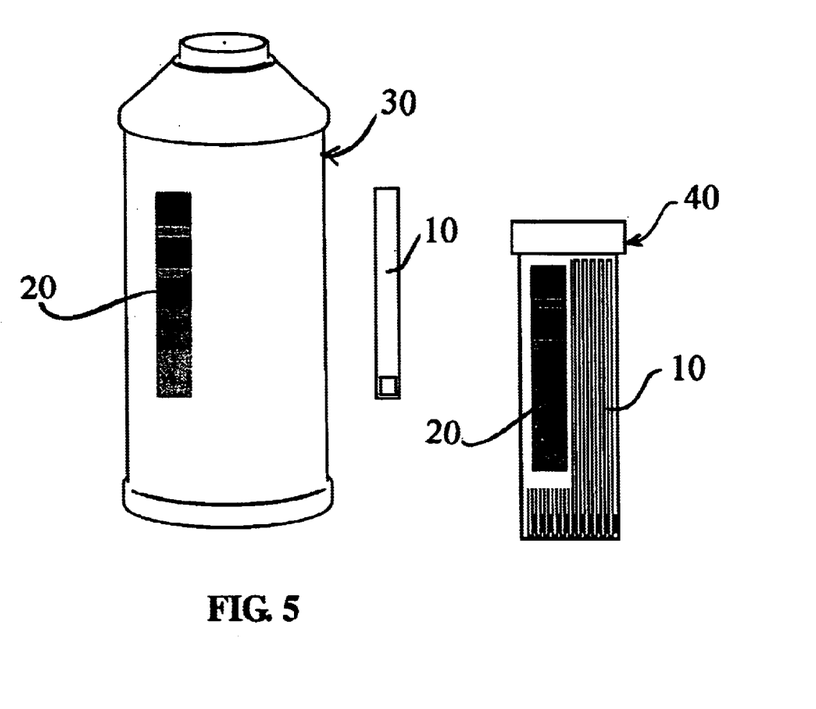
FIG. 5 is an illustration of a brake-fluid container including test strips and a color chart for testing brake fluid according to the invention.

As one skilled in the art would readily recognize, other devices are available to measure the content of a metal ion in a fluid. For example, ion-selective electrodes (such as marketed by Weiss Research Inc. of Houston, Tex., as part number Electrode P/N WCU1001) provide rapid measurements of ion concentrations in a fluid. Accordingly, such a device could be used in equivalent fashion to the procedure described above. For manual use, the readout of the device would be compared to a recommended maintenance threshold. In an automated system, the readout could be compared to the pre-set standards in a microprocessor to provide an appropriate instruction corresponding to the recommended maintenance action, if any. According to another aspect of the invention, test strips 10 are provided in a separate container 40 with a brake fluid bottle 30, as illustrated in FIG. 5, to encourage testing while adding fluid for maintenance purposes. A color standard patch 20 is also provided on both containers to conduct the test.

Figure 6:
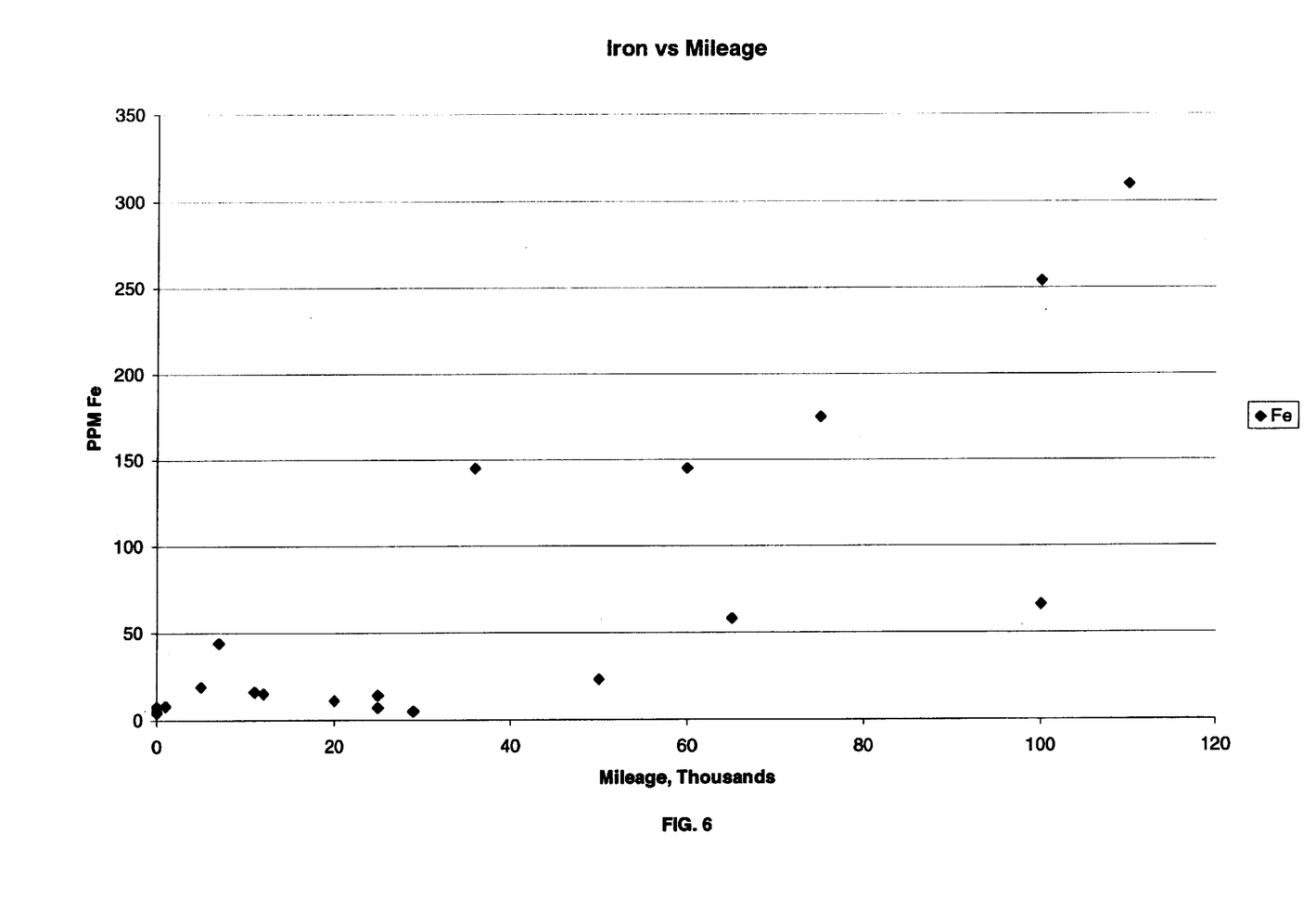
FIG. 6 is a plot showing the relationship between iron content and service mileage of brake fluid based on a variety of vehicles and commercial brake fluids.
Figure 7:
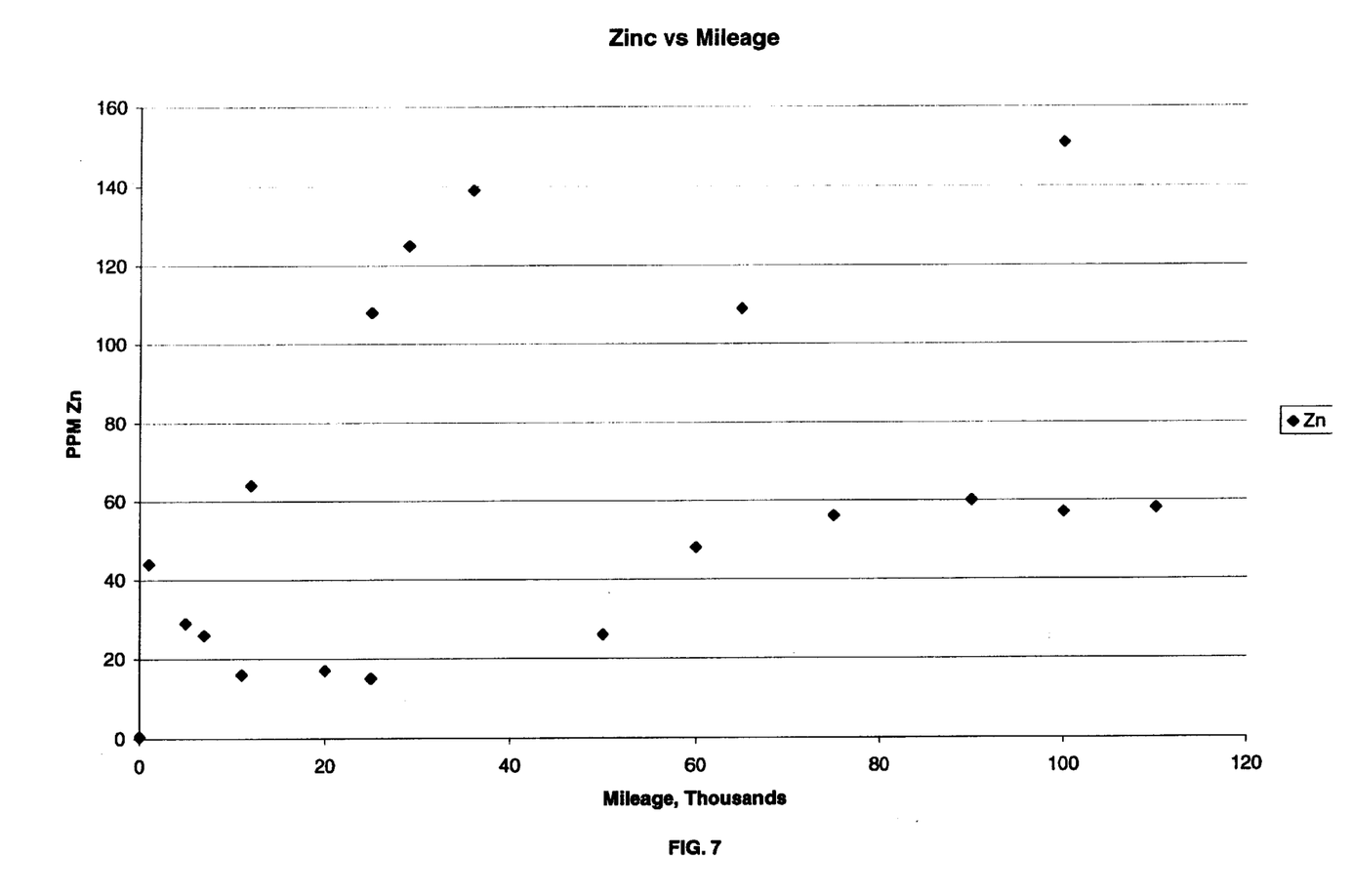
FIG. 7 is a plot showing the relationship between zinc content and service mileage of brake fluid based on a variety of vehicles and commercial brake fluids.
Figure 8:
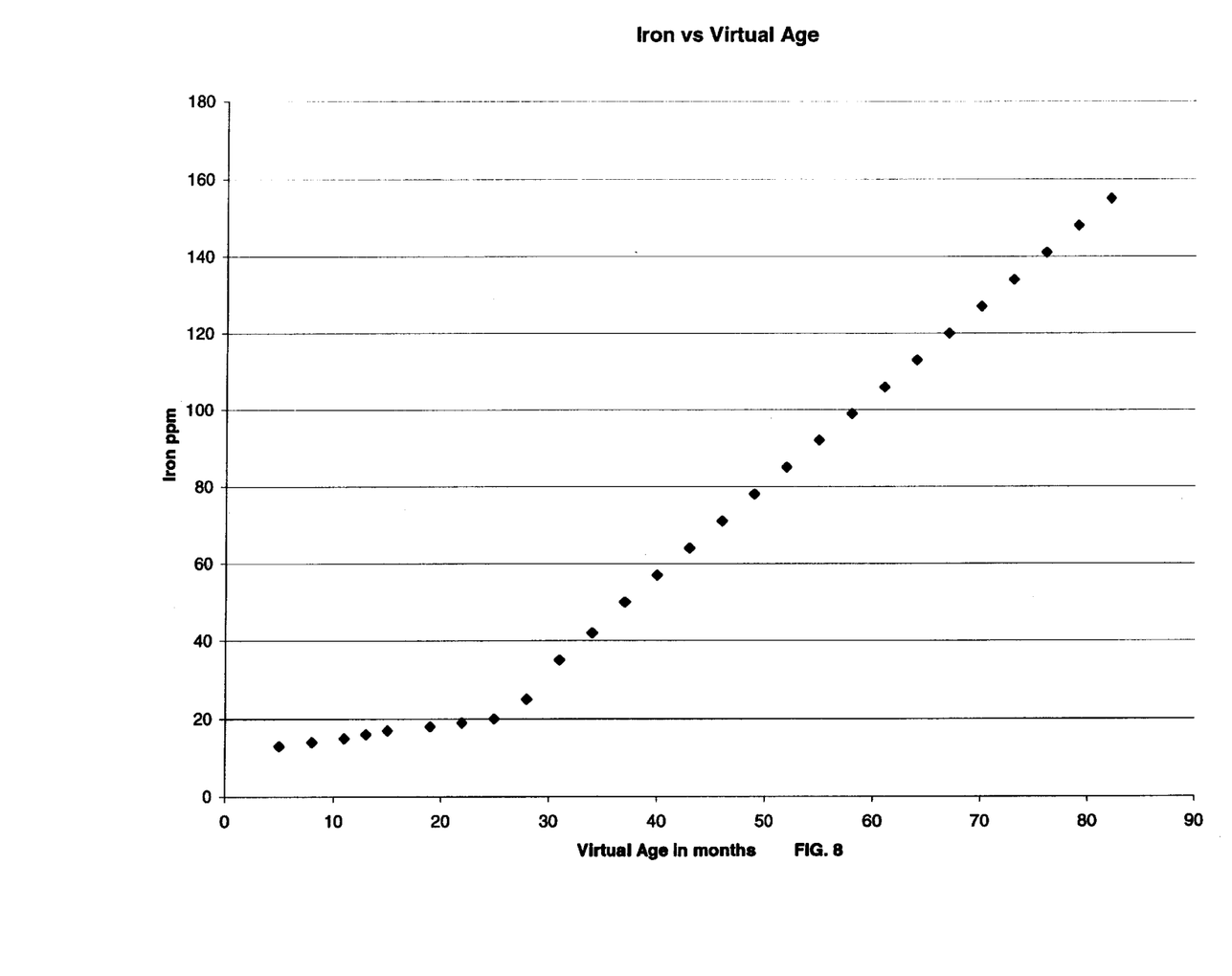
FIG. 8 is an empirically derived plot of brake-fluid iron content versus virtual age, used to estimate maintenance thresholds according to the invention.
Figure 9:
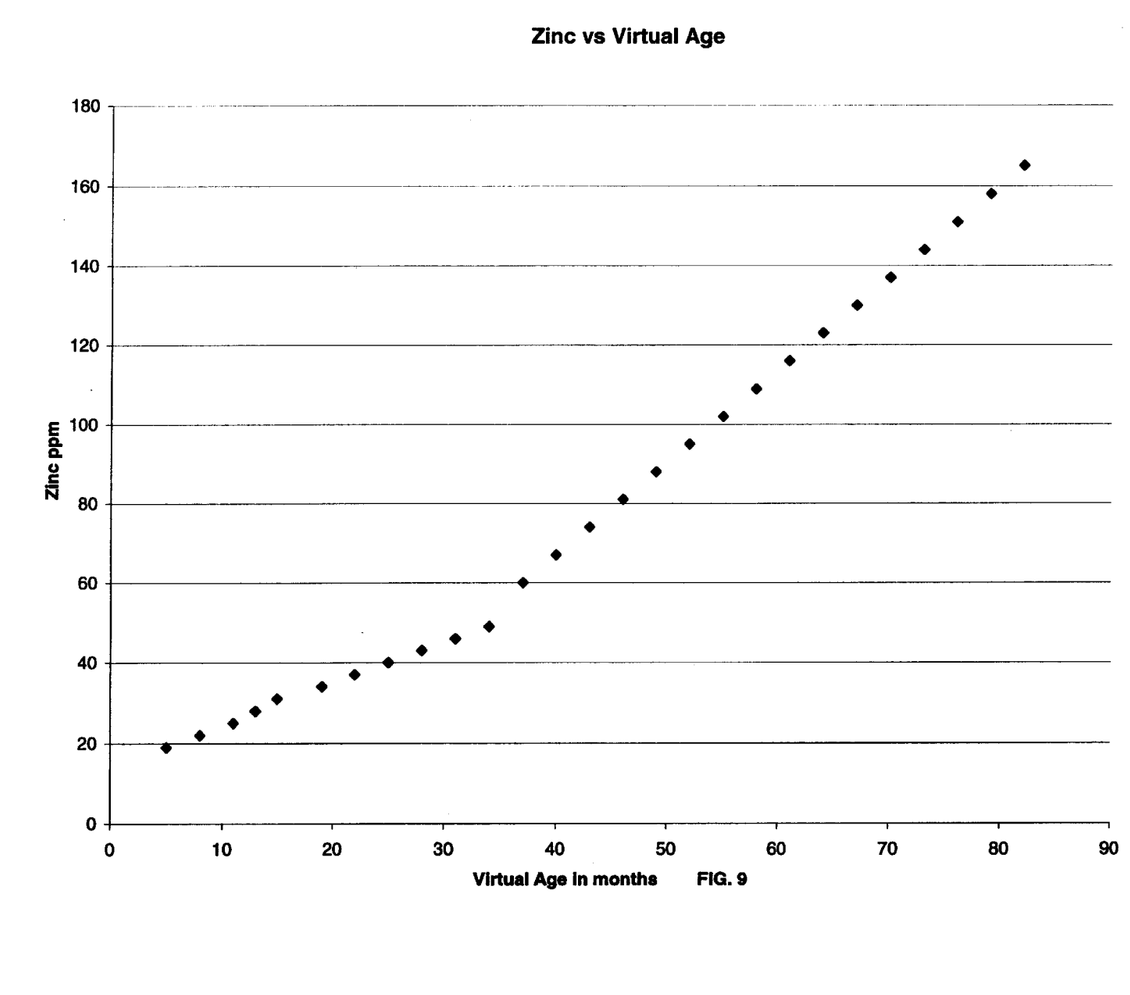
FIG. 9 is an empirically derived plot of brake-fluid zinc content versus virtual age, used to estimate maintenance thresholds according to the invention.

FIG. 1 shows that a similar correlation exists, albeit not as pronounced, between the contents of iron and zinc in brake fluid and its time of service. Accordingly, the development of a similar virtual-age versus metal-content correlation was investigated using the same methodology described for copper. FIGS. 6 and 7 are plots of metal-versus-mileage raw data for iron and zinc, respectively. FIGS. 8 and 9 are metal-versus-virtual age curves derived for iron and zinc, respectively, using the concept of the invention. The figures show that these curves can also be used to estimate maintenance thresholds as a function of the content of these metals in the brake fluid. For example, zinc values of about 50 ppm were found to correspond to a virtual age of 24 months, and iron values of about 50 ppm were found to correspond to a virtual age of 36 months. Accordingly, color strips, charts and test kits for each metal, as illustrated in FIGS. 4 and 5, are available for iron and zinc as well. Because of the more consistent correlation between copper and virtual age, though, copper is preferred to estimate maintenance milestones.

Iron is most suitable to determine when an unacceptable corrosive level has been reached in the brake fluid, regardless of its moisture or amine level. I found that any iron level above 50 ppm should be taken as a clear indicator of a corrosive condition. Therefore, the fluid should be replaced then irrespective of its copper content.

Thus, this invention provides an easy and accurate procedure for ascertaining the condition of brake fluid to effect the recommended maintenance of brake systems at the appropriate time as a function of actual wear and tear, rather than a prescribed schedule that may or may not reflect the actual condition of the fluid. The availability of this test may also encourage preventive maintenance, which is normally neglected with respect to brake fluid. While it is common practice to routinely change engine oil, transmission fluid, and all other fluids in a vehicle, brake fluid is rarely maintained unless a malfunction occurs. This is the case even though the brake system is critical to safety and brake fluid is known to deteriorate. This invention is directed at correcting this automotive maintenance shortcoming.

Since low moisture-absorption brake fluids have been introduced to the market, such as the product sold under the trademark CASTROL GT LMA, this invention provides a separate test, independent of moisture content, for assessing the need for fluid replacement in order to maintain a low level of corrosiveness in the brake system.

Various changes in the details, steps and components that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

I claim:

1. A method of establishing service requirements for a brake fluid in a vehicle's brake system as a function of a variable indicative of the fluid's service age and service mileage, comprising the following steps:
   (a) determining a correlation between said variable and a content of reactive constituent in the fluid;
   (b) measuring a current value of said content of reactive constituent in the fluid by reaction with a test reactant exposed to said brake fluid:
   (c) determining a current approximation of said variable on the basis of said correlation; and
   (d) carrying out a maintenance schedule for the brake system on the basis of said current approximation of the variable indicative of the fluid's service age and service mileage;
   wherein said reactive constituent is selected from the group consisting of copper, iron, and zinc.

2. The method of claim 1, wherein said test reactant includes a reactive strip and step (b) is carried out by immersing the strip in the fluid and by matching a color resulting thereby on the strip with a color chart representing a correlation between color and content of said reactive constituent in the fluid.

3. The method of claim 1, wherein said reactive constituent is copper, said test reactant includes a reactive copper strip and step (b) is carried out by immersing the strip in the fluid and by matching a color resulting thereby on the strip with a color chart representing a correlation between color and copper content in the fluid.

4. The method of claim 3, wherein said maintenance schedule includes an empirical copper-content threshold of 150 parts per million for replacement of the fluid.

5. The method of claim 1, wherein the reactive constituent is iron, said test reactant includes a reactive iron strip and step (b) is carried out by immersing the strip in the fluid and by matching a color resulting thereby on the strip with a color chart representing a correlation between color and iron content in the fluid.

6. The method of claim 5, wherein said maintenance schedule includes an empirical iron-content threshold of 50 parts per million for replacement of the fluid.

7. The method of claim 1, wherein the reactive constituent is zinc, said test reactant includes a reactive iron strip and step (b) is carried out by immersing the strip in the fluid and by matching a color resulting thereby on the strip with a color chart representing a correlation between color and zinc content in the fluid.

8. The method of claim 7, wherein said maintenance schedule includes an empirical zinc-content threshold of 50 parts per million for replacement of the fluid.

9. The method of claim 1, wherein an automated device is used in step (c).

10. The method of claim 1 wherein said brake system is an automotive brake system.

11. A kit for establishing service requirements for a brake fluid in a vehicle's brake system as a function of a variable indicative of the fluid's service age and service mileage, comprising:
   a test standard representing a correlation between said variable and a metal content in the brake fluid;
   a test reactant capable of reacting with said metal in the brake fluid and producing an indication of a current metal content in the brake fluid upon exposure of said test reactant with said brake fluid; and
   a predetermined empirical maintenance schedule for the brake system based on said variable indicative of the fluid's service age and service mileage;
   wherein said metal is selected from the group consisting of copper, iron, and zinc and said test standard includes a color chart.

12. The kit of claim 11, wherein said test reactant includes a reactive strip adapted for immersion in the fluid to produce said indication of a current metal content in the brake fluid.

13. The kit of claim 11 wherein said metal is copper, said test reactant includes a reactive copper strip, and said test standard includes a copper color chart.

14. The kit of claim 13, wherein said maintenance schedule includes an empirical threshold of 150 parts per million of copper for replacement of the fluid.

15. The kit of claim 11, wherein said reactive constituent is iron, said test reactant includes a reactive iron strip, and said test standard includes an iron color chart.

16. The kit of claim 15, wherein said maintenance schedule includes an empirical threshold of 50 parts per million of iron for replacement at the fluid.

17. The kit of claim 11, wherein said metal is zinc, said test reactant includes a reactive zinc strip, and said test standard includes a zinc color chart.

18. The kit of claim 11, further comprising an automated device for producing said indication of a current metal content in the fluid, and for establishing maintenance requirements for the brake fluid as a function of said current metal content in the fluid.

19. A brake-fluid dispenser and test kit for replacing brake fluid in a vehicle's brake system as a function of a variable indicative of the fluid's service age and service mileage, comprising:

a container with brake fluid;

a test standard representing a correlation between said variable and a metal content in the brake fluid;

a test reactant capable of reacting with said metal in the brake fluid and producing an indication of a current metal content in the brake fluid upon exposure of said test reactant with said wake fluid; and a predetermined empirical maintenance schedule for the brake system based on said variable indicative of the fluid's service age and service mileage;

wherein said metal is selected from the group consisting of copper, iron, and zinc and said test standard includes a color chart.

20. The kit of claim 19, wherein said test reactant includes a reactive strip adapted for immersion in the fluid to produce said indication of a current metal content in the fluid.

* * * * *

UNITED STATES PATENT AND TRADEMARK OFFICE
CERTIFICATE OF CORRECTION

PATENT NO.    : 6,691,562 B2
DATED         : February 17, 2004
INVENTOR(S)   : Jon A. Petty It is certified that error appears in the above-identified patent and that said Letters Patent is hereby corrected as shown below:

<u>Column 10,</u>
Line 11, change "wake" to -- brake --.

Signed and Sealed this

Twenty-first Day of June, 2005

JON W. DUDAS
*Director of the United States Patent and Trademark Office*